Figure 1:
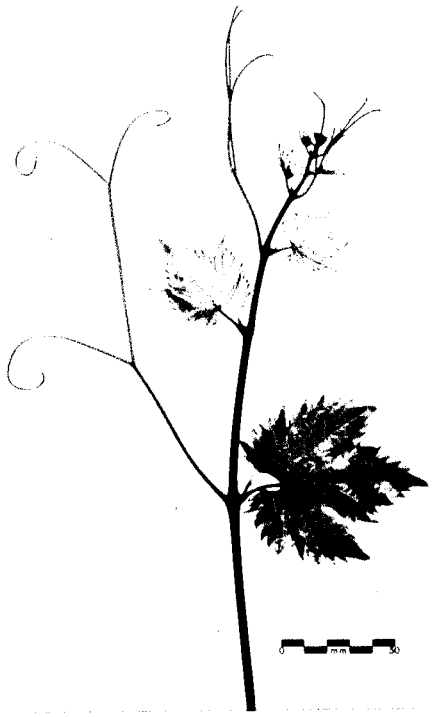

United States Patent [19]

Antcliff, deceased

[11] Patent Number: Plant 7,377

[45] Date of Patent: Nov. 6, 1990

[54] GRAPE VARIETY NAMED MARROO SEEDLESS

[75] Inventor: Allan J. Antcliff, deceased, late of Mildura, Australia, by Freda G. Antcliff, administrator

[73] Assignee: Commonwealth Scientific and Industrial Research Organization, Canberra, Australia

[21] Appl. No.: 301,990

[22] Filed: Jan. 25, 1989

[51] Int. Cl.[5] ..... A01H 5/00

[52] U.S. Cl. ..... Plt./47

[58] Field of Search ..... Plt./47

[56] References Cited

PUBLICATIONS

Clingeleffer, P. R. (1984), *First Table Grape Industry Technical Conference,* Leamon, K. (ed.), Agricultural Note Series 147, Dept. of Agriculture, Victoria, pp. 18–24.

Clingeleffer, P. R. (1985), *Aust. Grapegrower and Winemaker,* 256:117–119.

Clingeleffer, P. R. (1985), *Production, Promotion and Marketing of Western Australian Table Grapes: Proceedings of a Department of Agriculture Seminar,* Sep. 1985, Dept. of the Premier and Cabinet, Perth, Western Australia, pp. 9–17.

Clingeleffer, P. R. (1986), *Second National Table Grape Industry Technical Conference,* Geyle, A. (ed.) pp. 5–14.

Newman, H. P. and P. R. Clingeleffer (1987), *Food Technology in Australia,* 39:6, pp. 294–296.

Clingeleffer, P. R. (1987), *Achieving Quality—The Future of the Dried Vine Fruits Industry,* Jacka, L. and R. Johns (eds.), Dried Fruits Research Council Seminar, Conference Proceedings Series No. 15, Dept. of Agriculture and Rural Affairs, pp. 73–77.

Clingeleffer, P. R., Kerridge, G. H., Possingham, J. V. (1987), *The Eighth Viticulture Seminar,* Jul. 7–9, 1987, New England, Hunter and Metropolitan Region, Dept. of Agriculture, New South Wales, pp. 109–139.

Clingeleffer, P. R. and J. V. Possingham (1988), *Agricultural Science,* Feb./Mar. 1988, pp. 18–19.

*Primary Examiner*—James R. Feyrer

*Attorney, Agent, or Firm*—Greenlee and Associates

[57] ABSTRACT

A new and distinct variety of grapevine named Marroo Seedless having the characteristics of large, crisp and seedless berries with a pleasant, sweet taste, a uniform bunch shape; good vigor and production and the formation of large black berried seedless table grapes without the application of gibberellic acid to enhance berry size.

2 Drawing Sheets

The present invention comprises a new and distinct cultivar of grape, known by the cultivar name Marroo Seedless.

The new variety is the result of the following cross, Carolina Blackrose×Ruby Seedless made at the CSIRO Division of Horticulture.

The objectives in breeding this new variety were to combine the high productivity, large berry, good eating qualities and disease resistance of Carolina Blackrose with the seedless character, high vigour and productivity of Ruby Seedless.

It was selected from a progeny of 50 seedlings planted at the research station of the CSIRO Division of Horticulture, Merbein, Victoria, Australia in 1978. The new variety was then asexually reproduced from cuttings taken from the original seedling selection in winter 1982 and tested in field trials at the Merbein site, under the number, MS23-7. The variety was further tested at a regional level by State Departments of Agriculture and on selected grower properties. The unique features of the new variety have been retained.

Marroo Seedless has not been observed under all possible environmental conditions. The phenotype may vary significantly with variations in environment such as temperature, light intensity and day length.

The following traits have been repeatedly observed and are determined to be basic characteristics of Marroo Seedless, which in combination distinguish Marroo Seedless as a new and distinct cultivar.

(1) Large, black, crisp and seedless berry with a pleasant sweet taste;

(2) A uniform bunch shape;

(3) Good vigour and production;

(4) Production of large, black-berried seedless table grapes without application of gibberellic acid to enhance berry size.

The variety ripens early mid-season, about two weeks before its seedless parent, Ruby Seedless and is best adapted for culture under the same type of soil and climatic conditions.

Figure 2:
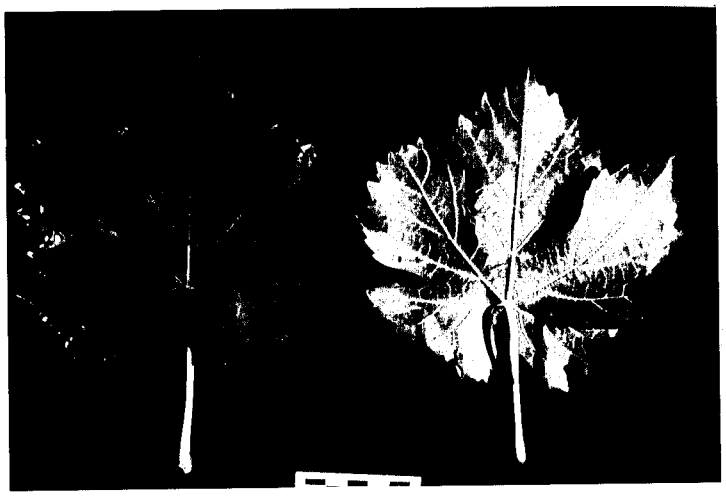
Figure 3:
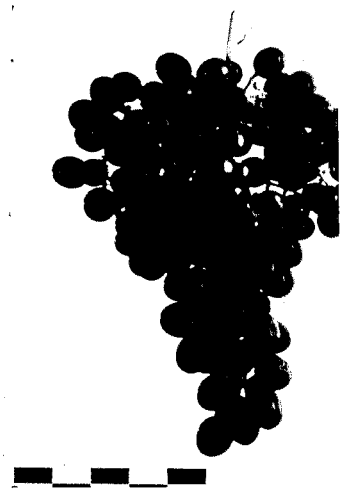
Figure 4:
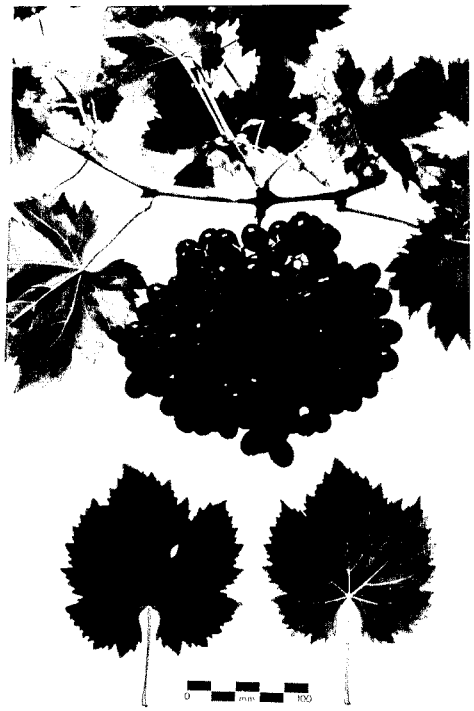

The accompanying photographic drawings illustrate characteristics of the Marroo Seedless wherein, FIG. 1 illustrates a typical shoot tip of this variety, FIG. 2 illustrates both the upper and lower surfaces of typical leaves, FIG. 3 illustrates a typical cluster of the new variety, without bunch trimming, and FIG. 4 illustrates a typical cluster of the new variety, after bunch trimming.

PLANT CHARACTERISTICS

The distinctive varietal characteristics of the novel plant described below in detail were observed during the first fruiting season and thereafter in trial plots at Merbein, Victoria, Australia, without the application of gibberellic acid.

Vine: Similar vigour to Ruby Seedless, with slender straight trunks, foliage canopy medium permitting uniform colouring of the fruit. Bud burst medium, at the same time as Ruby Seedless, leaf-fall medium, autumn coloration yellow-red.

Shoot-tip: (10"–12") Summit open, yellow-green, tinged bronze glabrous, shiny. First flat leaf 5-lobed, very shiny surface, lightly bronzed, tips shiny.

Shoot: Semi-erect habit, green with red stripes between nodes, nodes green vigorous, tendrils discontinuous, strong, bearing inflorescences at the 4th, 5th and 6th node, inflorescence medium width with strong, short peduncle, flower hermaphrodite, stamens diverging, filaments rigid.

Canes: Numerous canes, open, good wood maturity, reddish brown, smooth surface, lenticels absent, elliptic cross section, buds medium, "pointed" and sealed.

Leaf: Medium in size, short, pentagonal, upper surface medium green, hairless, involute, medium blistering on upper surface, teeth very long, straight sided, medium width petiolar sinus open, vee shaped, upper leaf sinuses slightly overlapping, the slightly reddened petiole shorter than main vein, no prostrate or erect hairs, resistant to downy mildew.

Cluster: Large, average 0.8–1.0 kg, 25 cm overall length from point of attachment, width 18 cm, peduncle short, 4.0 cm from attachment to first tendril branch, loose.

Berry: Medium, mean weight of 4.5–6.0 g; uniform in size, short elliptic, circular cross section; skin colour blue/black and uniform, medium bloom; flesh firm and juicy, not coloured, neutral flavour, expressed juice is clear; seedless with occasional lignified rudimentary seed; pedicel attachment to berry strong.

I claim:

1. The new and distinct variety of grapevine substantially as herein shown and described.

* * * * *